United States Patent
Ohnuki et al.

(10) Patent No.: US 9,302,980 B2
(45) Date of Patent: Apr. 5, 2016

(54) PROCESS FOR PRODUCING SOLID AMINO ACID

(71) Applicant: KANEKA CORPORATION, Osaka-shi (JP)

(72) Inventors: Masatoshi Ohnuki, Takasago (JP); Akira Nishiyama, Takasago (JP)

(73) Assignee: KANEKA CORPORATION, Osaka-shi (JP)

( * ) Notice: Subject to any disclaimer, the term of this patent is extended or adjusted under 35 U.S.C. 154(b) by 0 days.

(21) Appl. No.: 14/375,975

(22) PCT Filed: Jan. 21, 2013

(86) PCT No.: PCT/JP2013/051065
§ 371 (c)(1),
(2) Date: Jul. 31, 2014

(87) PCT Pub. No.: WO2013/114991
PCT Pub. Date: Aug. 8, 2013

(65) Prior Publication Data
US 2014/0343289 A1 Nov. 20, 2014

(30) Foreign Application Priority Data
Feb. 1, 2012 (JP) .................. 2012-020180

(51) Int. Cl.
*C07C 205/00* (2006.01)
*C07C 227/18* (2006.01)
*C07C 227/42* (2006.01)
*C07D 207/16* (2006.01)
*C07D 211/60* (2006.01)

(52) U.S. Cl.
CPC ............ *C07C 227/18* (2013.01); *C07C 227/42* (2013.01); *C07D 207/16* (2013.01); *C07D 211/60* (2013.01); *C07C 2101/02* (2013.01)

(58) Field of Classification Search
CPC .................................................. C07C 227/42
USPC ....................................................... 562/553
See application file for complete search history.

(56) References Cited

U.S. PATENT DOCUMENTS

| | | | |
|---|---|---|---|
| 6,072,083 | A | 6/2000 | Hasegawa et al. |
| 2005/0107473 | A1 | 5/2005 | Nagashima et al. |
| 2005/0197396 | A1 | 9/2005 | Hijiya et al. |

FOREIGN PATENT DOCUMENTS

| | | |
|---|---|---|
| CN | 102241555 A | 11/2011 |
| EP | 0861826 A1 | 9/1998 |
| EP | 1541546 A1 | 6/2005 |
| JP | 56 39792 | 4/1981 |
| JP | 57 156448 | 9/1982 |
| JP | 58 100687 | 6/1983 |
| JP | 58 209989 | 12/1983 |
| JP | 2003 183230 | 7/2003 |
| WO | 03 074470 | 9/2003 |

OTHER PUBLICATIONS

Nakajima et al. Tetrahedron, 1988, 44(3), 721-732.*
International Search Report Issued Mar. 19, 2013 in PCT/JP13/051065 Filed Jan. 21, 2013.
Extended European Search Report issued Jul. 31, 2015 in EP 13743938 filed Jan. 21, 2013.

* cited by examiner

*Primary Examiner* — Nizal Chandrakumar
(74) *Attorney, Agent, or Firm* — Oblon, McClelland, Maier & Neustadt, L.L.P.

(57) ABSTRACT

The problem to be solved by the present invention is to easily and efficiently produce an amino acid having 2 to 7 carbon atoms as a high-purity solid without complicated operation, which is useful as a synthetic intermediate for medicines or agrochemicals.

The present invention is characterized in comprising a step of precipitating solid amino acid with high purity. In the present invention, the by-produced salt composed of the sulfonic acid and the amine was removed to the mother liquor by reacting an amine with a sulfonic acid salt of amino acid in an aprotic polar solvent, or by reacting a sulfonic acid with an amine salt of amino acid in an aprotic polar solvent.

The sulfonic acid salt of amino acid, for example, may be produced by reacting a N-(tert-butoxycarbonyl) amino acid with a sulfonic acid, or by reacting an amino acid tert-butyl ester with a sulfonic acid.

6 Claims, No Drawings

PROCESS FOR PRODUCING SOLID AMINO ACID

TECHNICAL FIELD

The present invention relates to a process for producing an amino acid which is useful as a synthetic intermediate for medicines or agrochemicals, as a high-purity solid.

BACKGROUND ART

The following processes are known as a process for producing high-purity amino acid, A process of a process comprising steps of removing bacterial cells or the like from the amino acid produced with use of microorganisms through centrifugation, and being subjected to an ion-exchange resin (Patent Document 1), a process comprising steps of adding a salt to an alkali salt of amino acid and then being subjected to electrodialysis (Patent Document 2), a process comprising steps of recovering an amino acid salt from water or an alcohol solvent at the isoelectric point of amino acid (Patent Documents 3 and 4).

PRIOR ART DOCUMENTS

Patent Documents

Patent Document 1: JP-A-56-39792
Patent Document 2: JP-A-58-100687
Patent Document 3: JP-A-58-209989
Patent Document 4: JP-A-57-156448

SUMMARY OF THE INVENTION

Problems to be Solved by the Invention

However, many steps such as an adsorption step, a desorption step, a recovery step, and a concentration step are required in the process comprising the step of being subjected to an ion-exchange resin. The process comprising the step of being subjected to electrodialysis requires an expensive apparatus. Furthermore, these processes have a problem in that the concentration of a treatment solution is low, and the productivity is low. In addition, the process comprising the step of recovering an amino acid from water at the isoelectric point is generally difficult to apply to a low molecular weight amino acid having a high solubility in water. Similarly, the process comprising the step of recovering an amino acid from an alcohol solvent at the isoelectric point is difficult to apply to an amino acid having a high solubility in alcohol.

Solutions to the Problems

In view of the above, as a result of an earnest studies, the present inventors have finally found and completed a process for efficiently producing a high-purity solid amino acid, even when the amino acid has a high solubility in water, alcohol or the like.

That is, the present invention relates to a process for producing an amino acid which has 2 to 7 carbon atoms, comprising a step of precipitating solid amino acid by adding an amine to a sulfonic acid salt of amino acid in an aprotic polar solvent or by adding a sulfonic acid to an amine salt of amino acid in an aprotic polar solvent.

The above sulfonic acid salt of the amino acid, for example, may be produced by reacting a N-(tert-butoxycarbonyl) amino acid with a sulfonic acid in an aprotic polar solvent.

Additionally, the sulfonic acid salt of amino acid is also produced by reacting an amino acid tert-butyl ester with a sulfonic acid in an aprotic polar solvent.

The above amine salt of the amino acid, for example, may be produced by reacting an amino acid with an amine.

Effects of the Invention

According to the present invention, it is possible to easily and efficiently produce a high-purity solid of an amino acid which has 2 to 7 carbon atoms with a high solubility in water or alcohol by adding an amine to a sulfonic acid salt of the amino acid in an aprotic polar solvent, or by adding a sulfonic acid to an amine salt of the amino acid in an aprotic polar solvent.

MODE FOR CARRYING OUT THE INVENTION

Hereinbelow, the process according to the invention will be described in detail.

The amino acid produced in the present invention is an amino acid which has 2 to 7 carbon atoms. Preferable examples include α-amino acids such as glycine, alanine, 3,3,3-trifluoroalanine, 2-aminobutanoic acid, 2-amino-2-methylbutanoic acid, norvaline, 5,5,5-trifluoronorvaline, valine, 2-amino-4-pentenoic acid, 2-amino-2-methylpentenoic acid, propargylglycine, 2-amino-cyclopentanecarboxylic acid, norleucine, leucine, isoleucine, tert-leucine, 2-amino-4-fluoro-4-methylpentanoic acid, 4-aminocyclohexanecarboxylic acid, serine, O-methylserine, O-allylserine, threonine, homoserine, cysteine, 2-methylcysteine, methionine, penicillamine, aspartic acid, asparagine, glutamic acid, glutamine, 2-aminoadipic acid, ornithine, lysine, (1R,2S)-1-amino-2-vinyl-cyclopropanecarboxylic acid, (1R,2S)-1-amino-2-ethyl-cyclopropanecarboxylic acid, sarcosine, N-methylalanine and N,N-dimethylalanine; cyclic amino acids such as aziridinecarboxylic acid, azetidinecarboxylic acid, proline, 1-methylproline, 2-methylproline, 2-ethylproline, 3-methylproline, 4-methylproline, 5-methylproline, 4-methyleneproline, 4-hydroxyproline, 4-fluoroproline, pipecolic acid, nipecotic acid and isonipecotic acid; β-amino acids such as β-alanine, isoserine, 3-aminobutanoic acid, 3-aminopentanoic acid and β-leucine; and γ-amino acids such as 4-aminobutanoic acid, 4-amino-3-methylpropionic acid, 4-amino-3-propylbutanoic acid, 4-amino-3-isopropylbutanoic acid and 4-amino-2-hydroxybutanoic acid. Further the preferable amino acid is sarcosine, alanine, 2-amino-2-methylbutanoic acid, tert-leucine, proline, 2-methylpropline, pipecolic acid, nipecotic acid, or (1R,2S)-1-amino-2-vinyl-cyclopropanecarboxylic acid. Particularly, proline, pipecolic acid and sarcosine are most suitable for the present invention. The amino acid may be either a racemic or an optically active substance.

In the present invention, the number of carboxyl groups in one amino acid molecule is not particularly limited, and for example, the number may be one or may be a plural number. The number of amino groups per one amino acid molecule may also be, for example, one or a plural number. In addition, the number of carboxyl groups and the number of amino groups per one amino acid molecule may be different, but are preferably the same. The present invention is particularly preferable for neutral amino acids (for example, among amino acids described above, amino acids other than basic amino acids such as ornithine and lysine and acidic amino acids such as aspartic acid, glutamic acid and 2-aminoadipic acid).

The solid of the above amino acid can be efficiently produced by adding an amine to a sulfonic acid salt of the amino acid in an aprotic polar solvent.

The sulfonic acid salt of the amino acid used in the present invention may be one produced by any process, and is not particularly limited. For example, at least one of the amino group and the carboxyl group, preferably the amino group of the amino acid used as a raw material may be protected by a protecting group.

Examples of the protecting group of the amino group are those described in PEPTIDE GOUSEI NO KISO TO JIKKEN (basis and experiment of peptide synthesis), published by Maruzen Co., Ltd. (1985), PROTECTIVE GROUPS IN ORGANIC SYNTHESIS, the third edition, published by JOHN WILLY & SONS (1999) and the like. Among them, carbamate protecting groups such as a t-butoxycarbonyl (Boc) group and a benzyloxycarbonyl (Z) group are preferable. A t-butoxycarbonyl (Boc) group is particularly preferably used since deprotection is easy.

Examples of the protecting group of the carboxyl group include ester protecting groups such as a methyl ester group, an ethyl ester group and a t-butyl ester group; and amide protecting groups such as N-methylamide group, N-ethylamide group, N-benzylamide group and N,N-dimethylamide group. In the present invention, ester protecting groups may be preferably used, and among them, a methyl ester group, an ethyl ester group and a t-butyl ester group are preferred, and a t-butyl ester group is particularly preferred.

A production process of the sulfonic acid salt of the amino acid is not also particularly limited, and for example, the sulfonic acid salt may be produced by mixing the amino acid as a raw material with a sulfonic acid in an aprotic polar solvent. Particularly, when the raw material amino acid is protected by the above protecting group, it is desirable to mix the amino acid with a sulfonic acid in an aprotic polar solvent. When the protected amino acid and a sulfonic acid are mixed, dissociation of the protecting group and salt formation occur at the time. A solid of the amino acid can be precipitated from the reaction solution by adding an amine to a reaction solution after this deprotection and salt formation. Preferably, it is possible to react N-(tert-butoxycarbonyl)amino acid with a sulfonic acid to obtain a salt comprising the amino acid and the sulfonic acid, or to react amino acid tert-butyl ester with a sulfonic acid to obtain a sulfonic acid salt of the amino acid. At that time, the use of an aprotic polar solvent enables the use of the reaction solution as it is for precipitation of a solid without isolating the sulfonic acid salt of the amino acid.

The aprotic polar solvent used in producing the sulfonic acid salt of the amino acid is not particularly limited, but specific examples include ester solvents such as ethyl acetate, n-propyl acetate and isopropyl acetate; ether solvents such as tetrahydrofuran, diethyl ether, 1,4-dioxane, methyl tert-butyl ether, diisopropyl ether, ethylene glycol dimethyl ether (for example, diethylene glycol dimethyl ether); ketone solvents such as acetone and methyl ethyl ketone; nitrile solvents such as acetonitrile and propionitrile; halogen solvents such as methylene chloride, 1,2-dichloroethane and chlorobenzene; sulfoxide solvents such as dimethyl sulfoxide; amide solvents such as N,N-dimethylformamide and N,N-dimethylacetamide; urea solvents such as dimethylpropyleneurea; and triamide phosphonate solvents such as triamide hexamethylphosphonate. These solvents may be singly used, or two or more solvents may be used in combination. When two or more solvents are used in combination, the mixing ratio thereof is not particularly limited. In consideration of a load to the environment, it is also possible to use solvents except for halogen solvents, as these solvents. The solvent is preferably ethyl acetate, tetrahydrofuran, 1,4-dioxane, methylene chloride, 1,2-dichloroethane, acetonitrile, propionitrile, acetone, methyl ethyl ketone, ethylene glycol dimethyl ether, dimethyl sulfoxide, N,N-dimethylformamide or N,N-dimethylacetamide, more preferably methylene chloride, 1,2-dichloroethane, acetonitrile, acetone, N,N-dimethylformamide, N,N-dimethylacetamide, ethylene glycol dimethyl ether or dimethyl sulfoxide, further preferably methylene chloride, 1,2-dichloroethane, acetonitrile, acetone, N,N-dimethylformamide or N,N-dimethylacetamide, and particularly preferably methylene chloride or 1,2-dichloroethane.

From the viewpoint of cost and post-treatment, the upper limit of the use amount of the solvent is preferably 100 parts by weight, further preferably 50 parts by weight, and particularly preferably 20 parts by weight, relative to 1 part by weight of the N-(tert-butoxycarbonyl)amino acid or amino acid tert-butyl ester. The lower limit of the use amount of the solvent is preferably 0.1 parts by weight, further preferably 0.5 parts by weight, and particularly preferably 1 part by weight, relative to 1 part by weight of the N-(tert-butoxycarbonyl)amino acid or amino acid tert-butyl ester.

The sulfonic acid is preferably methanesulfonic acid, ethanesulfonic acid, trifluoromethanesulfonic acid, benzenesulfonic acid, p-toluenesulfonic acid, p-chlorobenzenesulfonic acid, p-nitrobenzenesulfonic acid or camphorsulfonic acid, further preferably methanesulfonic acid, p-toluenesulfonic acid or camphorsulfonic acid, and particularly preferably methanesulfonic acid. The pKa of the sulfonic acid may affect the purity or yield of the amino acid to be produced. Therefore, in order to produce amino acid in high purity and high yield, the sulfonic acid is, for example, preferably a sulfonic acid with a pKa of −5 to 2, and more preferably a sulfonic acid with a pKa of −4 to 1.

The use amount of the sulfonic acid is preferably 1 mol or more and further preferably 1.1 mol or more, relative to 1 mol of the N-(tert-butoxycarbonyl)amino acid or amino acid tert-butyl ester. However, in the case where the use amount is too large, such a case is not preferred from the viewpoint of cost and post-treatment. Thus, the upper limit of the use amount is preferably 10 mol or less and more preferably 5 mol or less.

The reaction temperature in the present reaction is not particularly limited and may be properly set, but the upper limit of the reaction temperature is preferably 120° C., further preferably 100° C., and particularly preferably 80° C. The lower limit of the reaction temperature is preferably −50° C., further preferably −30° C., and particularly preferably 0° C.

The reaction time in the present reaction is not particularly limited and may be properly set, but the upper limit of the reaction time is preferably 100 hours, further preferably 50 hours, and particularly preferably 20 hours. The lower limit of the reaction time is preferably 0.01 hours, further preferably 0.1 hours, and particularly preferably 1 hour.

Amine is added to the sulfonic acid salt of the amino acid produced as described above without isolation, whereby a solid of the amino acid can be precipitated. Further, when amine is added until pH reaches close to the isoelectric point of the amino acid, the solid of the amino acid can be efficiently precipitated. Regarding the sulfonic acid salt of the amino acid produced by other process, the solid of the amino acid can also be produced by adding an amine in an aprotic polar solvent.

The aprotic polar solvent includes the solvents as described above.

The amine is preferably methylamine, ethylamine, diethylamine, triethylamine, propylamine, diisopropylamine, diisopropylethylamine, tributylamine, N-methylmorpholine, pyridine, 4-dimethylaminopyridine, lutidine, ethylenediamine, N,N,N,N-tetramethylethylenediamine, ethanolamine, benzylamine or 1-phenethylamine, preferably triethylamine, diisopropylethylamine, N-methylmorpholine, pyridine or 1-phenethylamine, and particularly preferably triethylamine. As in the case of the sulfonic acid, the pKa of the amine may affect the purity or yield of the amino acid to be produced. Therefore, in order to produce amino acid in a high-purity and high yield, the amine is, for example, preferably an amine with a pKa of 7 to 15, and more preferably an amine with a pKa of 8 to 13.

In the present invention, a preferable embodiment of the combination of the sulfonic acid and the amine to be used is that at least one selected from methanesulfonic acid, p-toluenesulfonic acid and camphorsulfonic acid is used as the sulfonic acid, and at least one selected from triethylamine, diisopropylethylamine, N-methylmorpholine, pyridine and 1-phenethylamine is used as the amine. Particularly preferable embodiment is that the sulfonic acid is any one of methanesulfonic acid, p-toluenesulfonic acid and camphorsulfonic acid, and the amine is triethylamine. The combinations of the compounds described above makes it easier to form a salt when the sulfonic acid and the amine are brought into contact with each other. Thus, the solid of the amino acid is precipitated more easily.

The amine may be added while the pH being measured. When pH of the the isoelectric point of the amino acid is defined as pI, the pH may be roughly set within the range of pI value ±3. The upper limit of the pH is preferably +3, more preferably +2, and particularly preferably +1, relative to the isoelectric point (pH). The lower limit is preferably −3, more preferably −2, and particularly preferably −1, relative to the isoelectric point (pH).

Alternatively, the amine is preferably added in an amount that can neutralize the used sulfonic acid. The upper limit of the amount of the amine is preferably 1.8 mol, more preferably 1.5 mol, and particularly preferably 1.2 mol, relative to 1 mol of the sulfonic acid. The lower limit of the amount of the amine is preferably 0.3 mol, more preferably 0.5 mol, and particularly preferably 0.8 mol, relative to 1 mol of the sulfonic acid. The preferable embodiment is that the amine is used in a small excess amount of about 1 to 1.3 mol, relative to 1 mol of the sulfonic acid.

When the amine is added, the amine may be mixed with the sulfonic acid salt of the amino acid.

The temperature when adding is not particularly limited, and may be properly selected depending on the type of the solvent used, the target precipitation amount, and the quality of the solid. The upper limit of the temperature when adding is preferably 100° C., further preferably 80° C., and particularly preferably 60° C. The lower limit of the temperature when adding is preferably −60° C., further preferably −40° C., and particularly preferably −20° C.

When it is hard to precipitate the solid of the amino acid, or the precipitation amount of the solid is low, the mixture may be further cooled, concentrated, or a poor solvent may be added. Examples of the poor solvent include ethyl acetate, toluene, and hexane. These processes may be properly combined, and a solid may be added as a seed to precipitate the solid.

The precipitated solid of the amino acid can be separated and obtained by the process such as filtration under reduced pressure, filtration under applied pressure or centrifugation. In addition, when a mother liquor remains in the produced solid and the chemical purity is lowered, the solid is further washed with an aprotic polar solvent as necessary, whereby the quality may also be improved. From the viewpoint of more economically performing work, when producing the amino acid, it would be better to use the solvent which is the same as the solvent used in producing the sulfonic acid salt of the amino acid as the aprotic polar solvent. The process for drying the solid is not particularly limited, and it is desirable to dry the solid under reduced pressure (vacuum drying) at about 60° C. or less to avoid thermal decomposition and melting.

The solid of the amino acid can also be produced by adding a sulfonic acid to an amine salt of the amino acid in an aprotic polar solvent.

The amine salt of the amino acid used in the present invention may be one produced by any process, and is not particularly limited. For example, it is possible to produce the amine salt of the amino acid by reacting an amino acid with an amine. At that time, the use of an aprotic polar solvent enables the use of the reaction solution as it is for precipitation of a solid without isolating the amine salt of the amino acid.

As the conditions such as the type of the aprotic polar solvent used in producing the amine salt of the amino acid and the use amount of the solvent, the type of amine, a preferable combination of sulfonic acid and amine, the reaction temperature, and the reaction time are the same as in the case of the sulfonic acid salt of the amino acid.

The use amount of the amine is preferably 1 mol or more and further preferably 1.1 mol or more, relative to 1 mol of the amino acid. From the viewpoint of cost and post-treatment, however, in the case where the use amount is too large, such a case is not preferred. Thus, the upper limit of the use amount is preferably 10 mol or less, more preferably 5 mol or less.

When the amino acid has a plurality of unprotected carboxyl groups, the use amount of the amine may be set as the amount relative to 1 mol of the unprotected carboxyl group. The use amount of the amine may be within the same range as above, and thus the amine is preferably 1 mol or more and 10 mol or less, more preferably 1.1 mol or more and 5 mol or less, relative to 1 mol of the unprotected carboxyl group.

Sulfonic acid is added to the amine salt of the amino acid produced as described above without isolation, whereby a solid of the amino acid can be precipitated. Further, when sulfonic acid is added until pH reached close to the isoelectric point of the amino acid, the solid of the amino acid can be efficiently precipitated. Regarding the amine salt of the amino acid produced by other process, the solid of the amino acid can also be produced by adding sulfonic acid in an aprotic polar solvent.

The sulfonic acid used includes those used in producing the sulfonic acid salt of the amino acid.

The sulfonic acid is preferably added while the pH being measured. When pH of the the isoelectric point of the amino acid is defined as pI, the pH may be roughly set within the range of pI value ±3. The upper limit of the pH is preferably +3, more preferably +2, and particularly preferably +1, relative to the isoelectric point (pH). The lower limit is preferably −3, more preferably −2, and particularly preferably −1, relative to the isoelectric point (pH).

Alternatively, the sulfonic acid is preferably added in an amount that can neutralize the used amine. The upper limit of the amount of the sulfonic acid is preferably 1.8 mol, more preferably 1.5 mol, and particularly preferably 1.2 mol, relative to 1 mol of the amine. The lower limit of the amount of the sulfonic acid is preferably 0.3 mol, more preferably 0.5 mol, and particularly preferably 0.8 mol, relative to 1 mol of the amine.

When a sulfonic acid is added, a sulfonic acid may be mixed with the amine salt of the amino acid.

The temperature when adding and post-treatment are the same as in the case of producing an amino acid solid using the sulfonic acid salt of the amino acid.

In the present invention, it is important to add an amine or sulfonic acid to a sulfonic acid salt or an amine salt. According to the process of the present invention, it is possible to remove the by-produced salt composed of the sulfonic acid and the amine to the mother liquid, and to produce a solid of a high-purity amino acid. The present invention also enables a production of the solid of the amino acid in a high yield, for example, a yield of 30 to 100% (further, 50 to 100%).

This application claims the benefit of the right of priority based on Japanese Patent Application 2012-020180 filed on Feb. 1, 2012. The entire contents of the specification of Japanese Patent Application 2012-020180 filed on Feb. 1, 2012 are incorporated herein by reference.

EXAMPLES

Hereinbelow, the present invention will be described in further detail with reference to examples, but the present invention is not limited by these examples at all.

Examples 1 to 5, Comparative Examples 1 to 5

Triethylamine (607 mg, 6 mmol) was added to a solution of a methanesulfonic acid salt of amino acid (5 mmol), and solvent (5 mL, methanol or methylene chloride) at 25° C. In case where a solid was precipitated, the solution was stirred at 25° C. for 30 minutes after the solid was sufficiently precipitated. Thereafter, the solid was separated by filtration under reduced pressure, and was washed with the used solvent (5 mL), and was subjected to vacuum drying. The results (yields) of the operation with various amino acids are shown in the following table.

TABLE 1

|  | Amino acid | Solvent | Yield | Notes |
|---|---|---|---|---|
| Comparative example 1 | L-Proline | Methanol | — | Solid was not precipitated |
| Example 1 | L-Proline | Methylene chloride | 70% | — |
| Comparative example 2 | L-Alanine | Methanol | 100% | — |
| Example 2 | L-Alanine | Methylene chloride | 100% | — |
| Comparative example 3 | 4-Hydroxy-L-proline | Methanol | 100% | — |
| Example 3 | 4-Hydroxy-L-proline | Methylene chloride | 100% | — |
| Comparative example 4 | DL-Pipecolic acid | Methanol | 4% | — |
| Example 4 | DL-Pipecolic acid | Methylene chloride | 100% | — |
| Comparative example 5 | Sarcosine | Methanol | 43% | — |
| Example 5 | Sarcosine | Methylene chloride | 100% | — |

Comparative Example 6

Production of (S)-nipecotic acid

Methanesulfonic acid (576 mg, 6 mmol) was added to a solution of (S)—N-(tert-butoxycarbonyl)nipecotic acid (1145 mg, 5 mmol) and methanol (5 mL). When the mixture was stirred at 25° C. for 16 hours, (S)-methyl nipecotate was produced, and the object (S)-nipecotic acid was not produced.

Example 6

Production of (S)-nipecotic acid

Methanesulfonic acid (576 mg, 6 mmol) was added to a solution of (S)—N-(tert-butoxycarbonyl)nipecotic acid (1145 mg, 5 mmol) and methylene chloride (5 mL), and the mixture was stirred at 25° C. for 16 hours. Triethylamine (708 mg, 7 mmol) was added thereto, and then solid was precipitated. The solid was sufficiently precipitated, and then the solution was stirred at 25° C. for 30 minutes. Thereafter, the solid was separated by filtration under reduced pressure. The solid was washed with methylene chloride (5 mL), and then was subjected to vacuum drying. Thereby, the titled compound was produced as a white solid (238 mg, yield of 37%).

Titled Compound:

$^1$H-NMR (D$_2$O):

δ (ppm) 1.58 (m, 2H), 1.75 (m, 1H), 1.89 (m, 1H), 2.47 (m, 1H), 2.90-3.22 (m, 4H)

Example 7

Production Process of L-Proline

When triethylamine (607 mg, 6 mmol) was added to a solution of L-proline/(+)-10-camphor sulfonic acid salt (1731 mg, 5 mmol) and methylene chloride (5 mL), a solid was precipitated. The solid was sufficiently precipitated, and then the solution was stirred at 25° C. for 30 minutes. Thereafter, the solid was separated by filtration under reduced pressure. The solid was washed with methylene chloride (5 mL), and then was subjected to vacuum drying. Thereby, the titled compound was produced as a white solid (447 mg, yield of 78%).

Titled Compound:

$^1$H-NMR (D$_2$O): δ (ppm) 2.05 (m, 3H), 2.35 (m, 1H), 3.34-3.42 (m, 2H), 4.13 (m, 1H)

Example 8

Production of (1R,2S)-1-amino-2-vinyl-cyclopropanecarboxylic acid

Methanesulfonic acid (576 mg, 6 mmol) was added to a solution of (1R,2S)-1-(tert-butoxycarbonylamino)-2-vinyl-cyclopropanecarboxylic acid (1135 mg, 5 mmol) and methylene chloride (5 mL), and the mixture was stirred at 25° C. for 3 hours. When triethylamine (708 mg, 7 mmol) was added thereto, a solid was precipitated. The solid was sufficiently precipitated, and then the solution was stirred at 25° C. for 30 minutes. Thereafter, the solid was separated by filtration under reduced pressure. The solid was washed with methylene chloride (5 mL), and then was subjected to vacuum drying. Thereby, the titled compound was produced as a white solid (665 mg, yield of 100%).

Titled Compound:
$^1$H-NMR (D$_2$O): δ (ppm) 1.37 (m, 1H), 1.46 (m, 1H), 2.06 (s, 1H), 4.65 (s, 3H), 5.03 (m, 1H), 5.18 (m, 1H), 5.64 (m, 1H)

Example 9

Production of (S)-tert-leucine

Methanesulfonic acid (576 mg, 6 mmol) was added to a solution of (S)—N-(tert-butoxycarbonyl)-tert-leucine (1155 mg, 5 mmol) and methylene chloride (5 mL), and the mixture was stirred at 25° C. for 3 hours. When triethylamine (708 mg, 7 mmol) was added thereto, a solid was precipitated. The solid was sufficiently precipitated, and then the solution was stirred at 25° C. for 30 minutes and further stirred at 25° C. for 30 minutes. Thereafter, the solid was separated by filtration under reduced pressure. The solid was washed with methylene chloride (5 mL), and then was subjected to vacuum drying. Thereby, the titled compound was produced as a white solid (514 mg, yield of 75%).

Titled Compound:
$^1$H-NMR (D$_2$O): δ (ppm) 0.87 (s, 9H), 3.40 (s, 1H)

Example 10

Production of (S)-2-methylproline

Methanesulfonic acid (252 mg, 2.6 mmol) was added to a solution of (S)—N-(tert-butoxycarbonyl)-2-methylproline (500 mg, 2.2 mmol) and 1,2-dichloroethane (2.53 g), and the mixture was stirred at 25° C. for 3 hours. When triethylamine (265 mg, 2.6 mmol) was added thereto, a solid was precipitated. The solid was sufficiently precipitated, and then the solution was stirred at 25° C. for 30 minutes and further stirred at 25° C. for 2 hours. Thereafter, the solid was then separated by filtration under reduced pressure. The solid was washed with 1,2-dichloroethane (0.2 mL), and then was subjected to vacuum drying. Thereby, the titled compound was produced as a white solid (197 mg, yield of 69%).

Titled Compound:
$^1$H-NMR (D$_2$O):
δ (ppm) 1.59 (s, 3H), 1.95 (m, 2H), 2.07 (m, 1H), 2.34 (m, 1H), 3.33-3.45 (m, 2H)

Examples 11 to 17

Production of (S)-2-methylproline

The same operations were carried out by replacing the solvent, acid and base of Example 10 with the conditions listed below.

Example 18

Production of (S)-2-methylproline

When methanesulfonic acid (65 mg, 0.7 mmol) was added to a solution of (S)-phenethylamine salt (92 mg, 0.7 mmol) of (S)-2-methylproline and N,N-dimethylacetamide (0.81 g), a solid was precipitated. The solid was sufficiently precipitated, and then the solution was stirred at 25° C. for 1 hour. Thereafter, the solid was separated by filtration under reduced pressure. The solid was washed with N,N-dimethylacetamide (0.4 mL), and then was subjected to vacuum drying. Thereby, the titled compound was produced as a white solid (85 mg, yield of 97%).

Example 19

Production of (R)-2-amino-2-methylbutanoic acid

Methanesulfonic acid (85 mg, 0.9 mmol) was added to a solution of (R)-2-amino-2-methylbutanoic acid tert-butyl ester (151 mg, 0.7 mmol) and 1,2-dichloroethane (0.81 g), and the mixture was stirred at 25° C. for 3 hours and further at 80° C. for 10 hours. The mixture was cooled to 25° C. Thereafter, when a solution of triethylamine (92 mg, 0.9 mmol) and 1,2-dichloroethane (1.62 g) was added thereto, a solid was precipitated. The solution was stirred at 25° C. for 16 hours, and then the solid was separated by filtration under reduced pressure. The solid was washed with 1,2-dichloroethane (0.4 mL), and then was subjected to vacuum drying. Thereby, the titled compound was produced as a white solid (86 mg, yield of 76%).
$^1$H-NMR (D$_2$O): δ (ppm) 0.77 (t, 3H), 1.32 (s, 3H), 1.61 (m, 1H), 1.76 (m, 1H)

Example 20

Production of DL-2-amino-2-methylbutanoic acid

Methanesulfonic acid (430 mg, 4.5 mmol) was added to a solution of N-(tert-butoxycarbonyl)-2-amino-2-methylbutanoic acid (866 mg, 3.7 mmol) and methylene chloride (7 mL), and the mixture was stirred at 25° C. for 30 minutes. When triethylamine (491 mg, 4.8 mmol) was added thereto, a solid was precipitated.
The solid was sufficiently precipitated, and then the solution was stirred at 25° C. for 10 minutes. Thereafter, the solid was separated by filtration under reduced pressure. The solid was washed with methylene chloride (14 mL), and then was subjected to vacuum drying. Thereby, the titled compound was produced as a white solid (464 mg, yield of 100%).

TABLE 2

|  | Solvent | Acid | Amine | Yield |
| --- | --- | --- | --- | --- |
| Example 11 | Acetone | Methanesulfonic acid | Triethylamine | 100% |
| Example 12 | Acetonitrile | Methanesulfonic acid | Triethylamine | 88% |
| Example 13 | N,N-Dimethylacetamide | Methanesulfonic acid | Triethylamine | 97% |
| Example 14 | Dimethyl sulfoxide | Methanesulfonic acid | Triethylamine | 77% |
| Example 15 | Diethylene glycol dimethyl ether | Methanesulfonic acid | Triethylamine | 69% |
| Example 16 | N,N-dimethylacetamide | p-Toluenesulfonic acid | Triethylamine | 95% |
| Example 17 | Dimethyl sulfoxide | Methanesulfonic acid | 4-Dimethylaminopyridine | 49% |

The invention claimed is:

1. A process for producing an unprotected amino acid comprising 2 to 7 carbon atoms, the process comprising
   precipitating a solid of the unprotected amino acid
      wherein the precipitating is carried out by adding an amine to a sulfonic acid salt of an unprotected amino acid in an aprotic polar solvent, adding an amine to a sulfonic acid salt of an amino acid produced by reacting a N-(tert-butoxycarbonyl) amino acid with a sulfonic acid in an aprotic polar solvent, adding an amine to a sulfonic acid salt of an amino acid produced by reacting an amino acid tert-butyl ester with a sulfonic acid in an aprotic polar solvent or
   by adding a sulfonic acid to an amine salt of an unprotected amino acid in an aprotic polar solvent,
      wherein optionally the addition of the amine or the sulfonic acid continues until pH of a solution comprising the sulfonic acid salt or the amine salt reaches a range of isoelectric point of the amino acid pI value ±3.

2. The process according to claim 1, wherein the aprotic polar solvent is at least one selected from the group consisting of methylene chloride, 1,2-dichloroethane, acetonitrile, acetone, N,N-dimethylformamide, N,N-dimethylacetamide, ethylene glycol dimethyl ether and dimethyl sulfoxide.

3. The process according to claim 1, wherein:
   the sulfonic acid is at least one selected from the group consisting of methanesulfonic acid, p-toluenesulfonic acid, and camphorsulfonic acid; and
   the amine is triethylamine.

4. The process according to claim 1, wherein the amino acid is at least one selected from the group consisting of sarcosine, alanine, 2-amino-2-methylbutanoic acid, tert-leucine, proline, 2-methyl proline, pipecolic acid, nipecotic acid and (1R,2S)-1-amino-2-vinyl-cyclopropanecarboxylic acid.

5. The process according to claim 1, wherein the process comprises precipitating the solid of the unprotected amino acid by adding the amine to the sulfonic acid salt of the amino acid in the aprotic polar solvent.

6. The process according to claim 1, wherein the process comprises precipitating the solid of the unprotected amino acid by adding the sulfonic acid to the amine salt of amino acid in the aprotic polar solvent.

* * * * *